(12) United States Patent
Sonderegger

(10) Patent No.: US 12,171,982 B2
(45) Date of Patent: Dec. 24, 2024

(54) SUBCUTANEOUS INFUSION NEEDLE STICK PREVENTION DEVICE USING NEEDLE HUB RETRACTION

(71) Applicant: Becton, Dickinson and Company, Franklin Lakes, NJ (US)

(72) Inventor: Ralph Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/134,148

(22) Filed: Apr. 13, 2023

(65) Prior Publication Data

US 2023/0241312 A1 Aug. 3, 2023

Related U.S. Application Data

(62) Division of application No. 16/329,651, filed as application No. PCT/US2017/051600 on Sep. 14, 2017, now Pat. No. 11,628,248.

(Continued)

(51) Int. Cl.
*A61M 5/158* (2006.01)
*A61M 5/162* (2006.01)

(52) U.S. Cl.
CPC .......... *A61M 5/158* (2013.01); *A61M 5/1626* (2013.01); *A61M 2005/1583* (2013.01);

(Continued)

(58) Field of Classification Search
CPC ...... A61M 5/158; A61M 5/1626; A61M 5/32; A61M 5/3205; A61M 5/3206; A61M 5/321; A61M 5/322; A61M 5/3221; A61M 5/3232; A61M 2005/14252; A61M 2005/14256; A61M 2005/1426; A61M 2005/1583; A61M 2005/1585;

(Continued)

(56) References Cited

U.S. PATENT DOCUMENTS 4,747,831 A 5/1988 Kulli
4,757,831 A 5/1988 Kulli
(Continued)

FOREIGN PATENT DOCUMENTS

JP 2004-524926 A 8/2004
JP 2007-296022 A 11/2007
(Continued)

*Primary Examiner* — Kami A Bosworth
(74) *Attorney, Agent, or Firm* — Dickinson Wright PLLC

(57) ABSTRACT

A needle stick prevention device (10, 110) includes a needle shield (20, 120) for selectively covering a distal end of a needle (41, 141). A needle hub (40, 140) is movably received within the needle shield (20, 120). The needle hub (40, 140) includes a proximal end (42, 142), a distal end (46, 146), a needle (41, 141) fixedly connected to the distal end of the needle hub (40, 140), and a plurality of ribs (54) or a cylinder (150) disposed between the proximal and distal ends. An actuation button movably received in a transverse opening of the needle shield (20, 120) to engage the needle shield (20, 120), the needle hub (40, 140) and a medical device. A spring (58, 158) is disposed between the needle hub (40, 140) and actuation member to automatically retract the needle (41, 141) into the needle shield (20, 120).

8 Claims, 15 Drawing Sheets

Related U.S. Application Data

(60) Provisional application No. 62/395,200, filed on Sep. 15, 2016.

(52) U.S. Cl.
CPC ............... *A61M 2005/1585* (2013.01); *A61M 2005/1586* (2013.01); *A61M 2005/1587* (2013.01)

(58) Field of Classification Search
CPC .. A61M 2005/1586; A61M 2005/1587; A61M 2005/3228; A61M 2005/3236; A61M 2039/0291
See application file for complete search history.

(56) References Cited

U.S. PATENT DOCUMENTS

| | | |
|---|---|---|
| 5,575,777 A | 11/1996 | Cover et al. |
| 5,885,257 A | 3/1999 | Badger |
| 6,090,078 A | 7/2000 | Erskine |
| 6,123,688 A | 9/2000 | Botich et al. |
| 6,641,555 B1 | 11/2003 | Botich et al. |
| 2004/0158207 A1 | 8/2004 | Hunn et al. |
| 2007/0185454 A1 | 8/2007 | Fangrow, Jr. |
| 2008/0208139 A1* | 8/2008 | Scheurer ............... A61M 5/158 604/192 |
| 2008/0228144 A1* | 9/2008 | Liniger ................. A61M 5/158 604/164.08 |
| 2008/0249473 A1 | 10/2008 | Rutti et al. |
| 2009/0069750 A1* | 3/2009 | Schraga ............ A61M 5/14248 604/539 |
| 2009/0299301 A1 | 12/2009 | Gottlieb et al. |
| 2011/0040263 A1* | 2/2011 | Hordum ............ A61M 5/14248 604/272 |
| 2011/0060287 A1* | 3/2011 | Ambruzs ............... A61M 5/158 604/164.12 |
| 2011/0213340 A1* | 9/2011 | Howell ................. A61M 5/158 604/533 |
| 2014/0088509 A1 | 3/2014 | Sonderegger et al. |
| 2014/0336583 A1 | 11/2014 | Morrissey et al. |

FOREIGN PATENT DOCUMENTS

| | | |
|---|---|---|
| JP | 2015-500100 A | 1/2015 |
| WO | WO2013086439 A1 | 6/2013 |

\* cited by examiner

SUBCUTANEOUS INFUSION NEEDLE STICK PREVENTION DEVICE USING NEEDLE HUB RETRACTION

This application is a division of U.S. patent application Ser. No. 16/329,651, filed on Feb. 28, 2019, which is the U.S. national stage of International Patent Application No. PCT/US2017/051600, filed Sep. 14, 2017, which claims priority under 35 U.S.C. § 119(e) from U.S. Provisional Application Ser. No. 62/395,200, filed on Sep. 15, 2016, each of which is incorporated herein by reference in its entirety.

FIELD OF THE INVENTION

The present invention relates to needle stick prevention devices, and more particularly, to a needle stick prevention device with automatic needle retraction.

BACKGROUND OF THE INVENTION

Needle sharps safety is a growing and important aspect of medical devices. Regulatory and market forces have both driven the need for a reliable way of protecting health-care professionals, custodial personnel and users from needle stick injury. The ability to protect users and personnel from needle stick injury is a critical aspect that influences the market success of a medical device.

The introduction of fluids into a patient using a catheter and insertion device is known. For intravenous infusion, a common insertion device is a syringe with an introducer needle received in a catheter. Currently there are several devices that prevent needle stick injury and enable the safe disposal of an introducer needle. These devices are often complicated, expensive and/or difficult to manufacture. Additionally, some previous devices have shown actuation inconsistencies throughout their operating window.

As such, it may be appreciated that there is a continuing need for a new and improved needle stick prevention device for an insertion needle that addresses the problems noted above and is simple and low-cost to manufacture. Embodiments of the present invention substantially fulfill this need.

SUMMARY OF THE INVENTION

In accordance with an aspect of the present invention, a needle stick prevention device is provided for use with a medical device including a base, the base having a column extending proximally from the base, and a head extending from the column forming an undercut between the base and the head. The needle stick prevention device comprises a needle shield for selectively covering a distal end of a needle including an outer wall with a passageway communicating with a proximal end and a distal end, wherein the proximal end includes a proximal opening and the distal end includes a transverse opening communicating with a distal opening extending through the distal end; a needle hub movably received within the passageway of the needle shield, the needle hub including a proximal end, a distal end, a needle fixedly connected to the distal end of the needle hub, and an actuation button movably received in the transverse opening of the needle shield to selectively engage the needle shield, the needle hub and the medical device; and a spring disposed between the needle hub and actuation member, wherein in a first state, the spring is held in a compressed state between the needle hub and actuation member and the medical device is releasably locked with the actuation button, and in a second state after the actuation button is actuated, the actuation button is removable from the medical device, the spring is released, and the needle hub is movable relative to the needle shield.

In accordance with another aspect of the present invention, a needle stick prevention device is provided for use with a medical device including a base, the base having a column extending proximally from the base, and a head extending from the column forming an undercut between the base and the head. The needle stick prevention device comprises a needle shield for selectively covering a distal end of a needle including an outer wall with a passageway communicating with a proximal end and a distal end, wherein the proximal end includes a proximal opening and the distal end includes a transverse receptacle communicating with a distal opening extending through the distal end; a needle hub movably received within the passageway of the needle shield, the needle hub including a proximal end, a distal end, a needle fixedly connected to the distal end of the needle hub, an a transverse opening disposed proximal to the distal end; an actuation plug movably received in the transverse opening of the needle hub and the transverse receptacle of the needle shield to engage the needle shield, the needle hub and the medical device; and a spring disposed between the needle hub and actuation plug, wherein in a first state the spring is held in a compressed state between the needle hub and actuation plug, the needle hub is not movable relative to the needle shield and the medical device is releasably locked with the actuation plug, and in a second state after the actuation plug is advanced into the transverse receptacle, the actuation plug is removable from the medical device, the spring is released, and the needle hub is movable relative to the needle shield.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
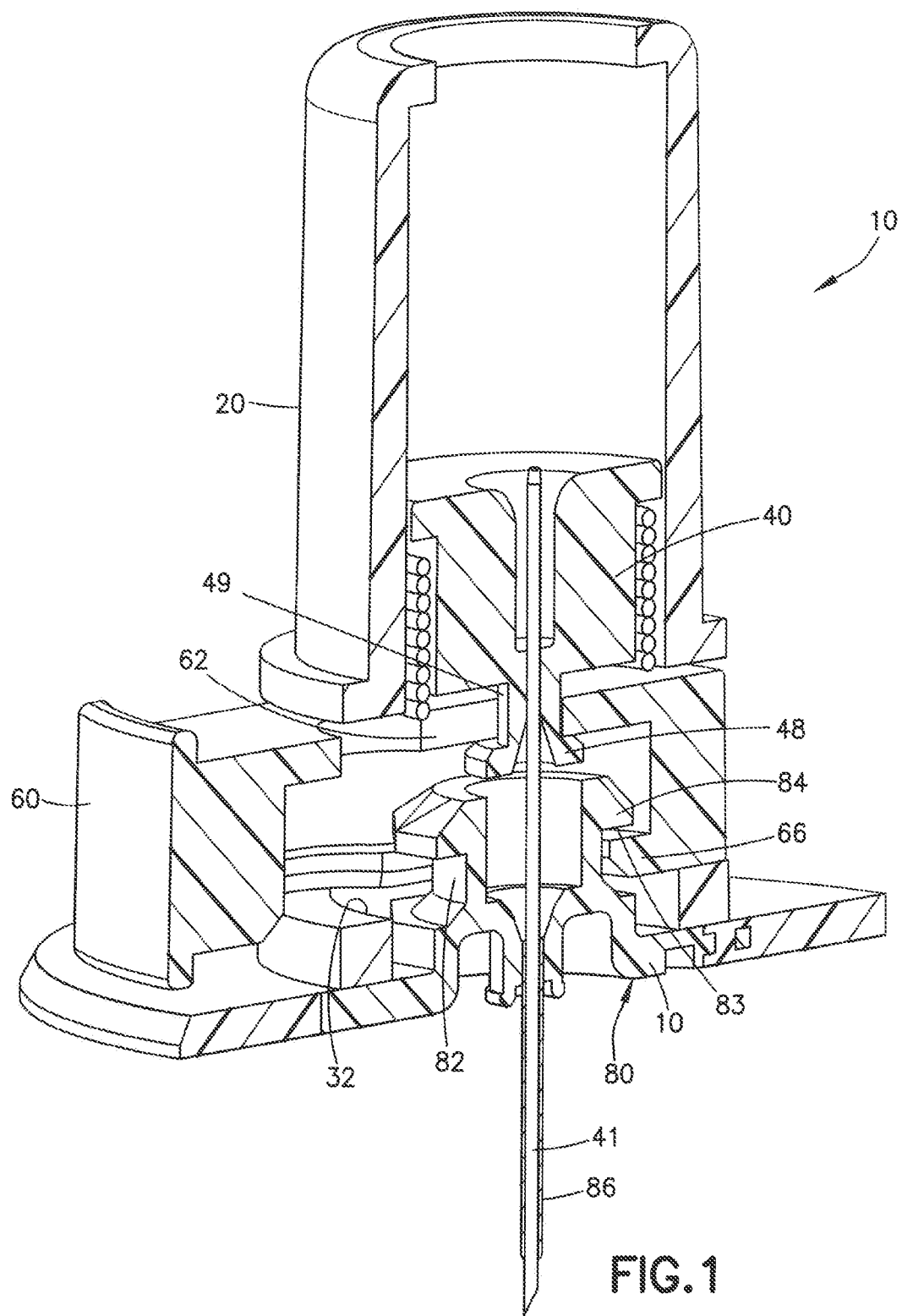
FIG. 1 is a cross-sectional view of a needle stick prevention device for an insertion needle, and an infusion set base in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit the present invention by referring to the drawings.

It will be understood by one skilled in the art that this disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

An infusion set assembly comprising a base 80 and a needle stick prevention device 10 are shown in FIG. 1. The infusion set base 80 has a column 82 affixed thereto and a head 84 disposed on the column. An actuation plug or button 60 of the needle stick prevention device 10 engages with a needle shield 20, a needle hub 40 and the base 80 via a transverse opening 32 formed in the needle shield 20. The actuation button 60 includes dual keyhole shaped openings 64 that allow a needle 41 and the needle hub 40 to extend through the actuation button 60.

Figure 2:
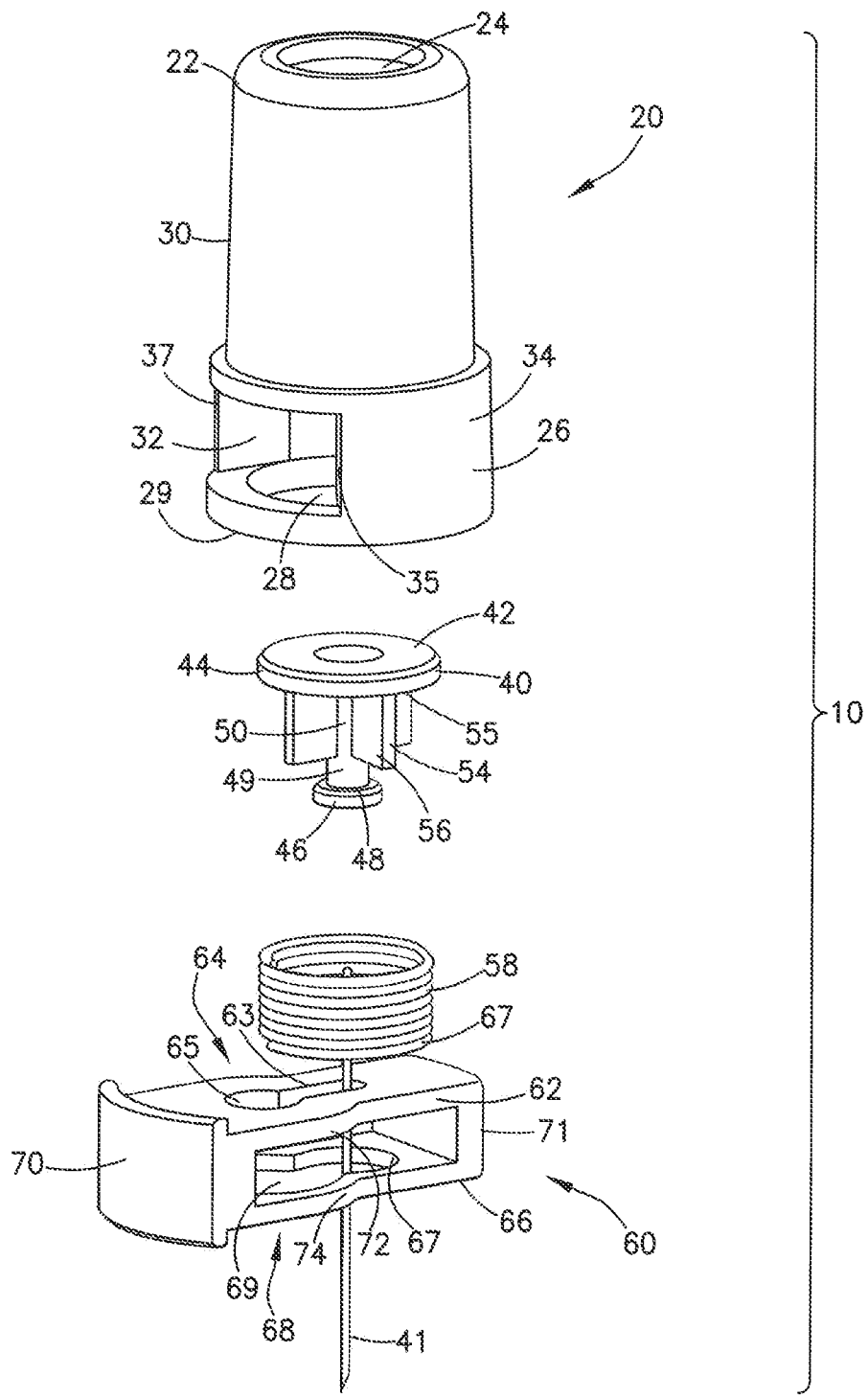
FIG. 2 is an exploded perspective view of the needle stick prevention device of FIG. 1.

FIG. 2 illustrates an exploded view of the needle stick prevention device 10. As shown, the needle shield 20 for selectively covering a distal end of a needle 41 includes a circumferential outer wall 30 with a proximal end 22 and a distal end 26. The proximal end 22 includes a proximal opening 24 and the distal end 26 includes a distal surface 29 with a distal opening 28 extending therethrough. A passageway 33 is formed by the outer wall 30 and extends between the proximal opening 24 and the distal opening 28.

Formed on the outer surface of the needle shield 20 is a radially extending ridge 34 to limit lateral movement of an actuation button 60. The transverse opening 32 is formed in the ridge 34 of the outer wall 30 proximal to the distal surface 29.

Movably received within the needle shield passageway 33 is a needle hub 40. The needle hub 40 includes a proximal end 42 and a distal end 46 with a hub body 50 extending therebetween. According to one embodiment, the needle 41 is received in an inner passageway 57 of the hub body 50. As shown in FIG. 2, the needle hub 40 also includes a collar 44 located at the proximal end 42 and a flange 48 located at the distal end 46. A plurality of ribs 54 extends radially from the hub body 50 between the collar 44 and the flange 48. Each of the plurality of ribs includes a proximal end 55 and a distal end 56. A recess 49 is formed between the distal end 56 of plurality of ribs and the flange 48.

Figure 5:
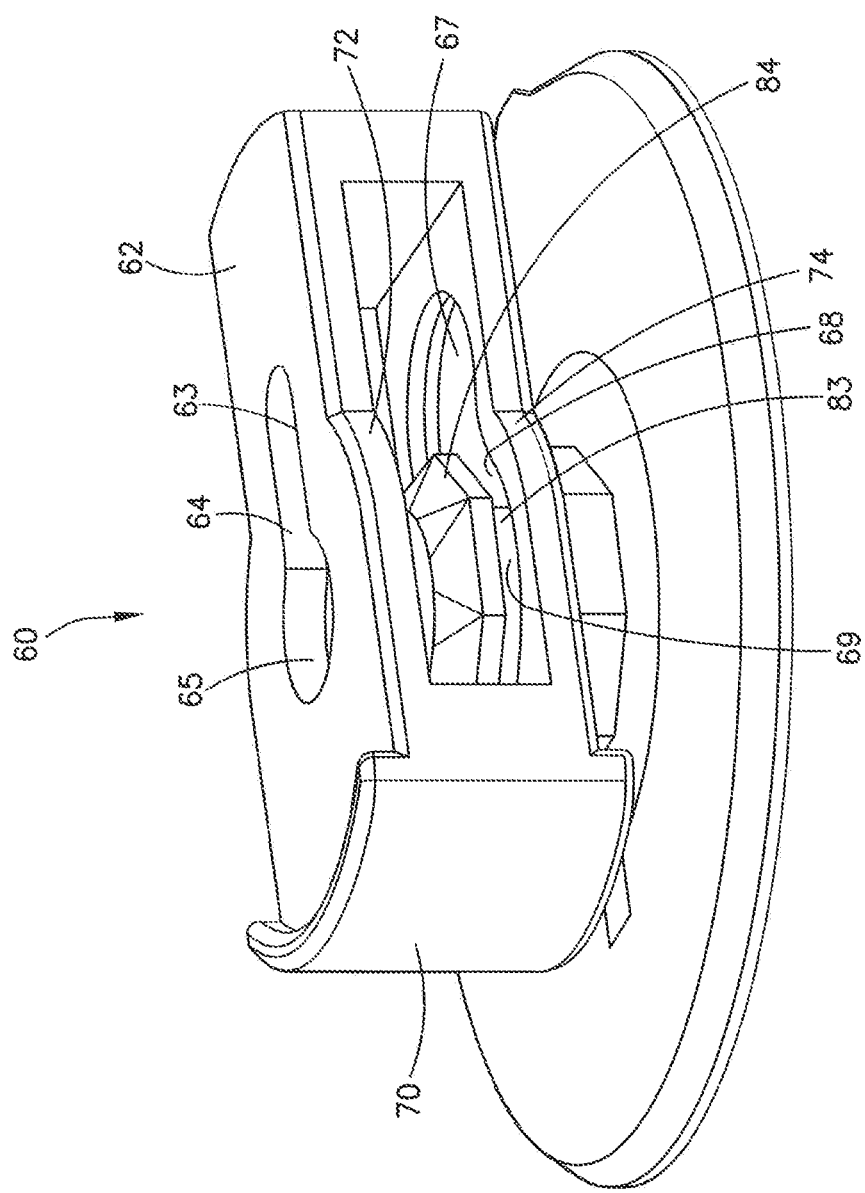
FIG. 5 is a perspective view of an actuation button of the needle stick prevention device of FIG. 1 and the base of FIG. 1.

As illustrated in FIGS. 2 and 5, the actuation button 60 includes an upper latch 62 and a lower latch 66 joined at a first end by a button head 70 including a user actuation surface and joined at a second end by a wall 71. The upper latch 62 and lower latch 66 extend laterally between the button head 70 and wall 71. The upper latch 62 includes a first key hole 64 with a locking portion 63 and an unlocking portion 65. The locking portion 63 is smaller than the unlocking portion 65. The lower latch 66 includes a second key hole 68 with a locking portion 67 and an unlocking portion 69. The unlocking portion 69 is larger than the locking portion 67. The upper and lower latches 62, 66 also include upper and lower protrusion portions 72, 74 respectively.

Referring back to FIG. 1, the infusion set base 80 can be removably engaged with the actuation button 60 via an undercut 83 formed between the column 82 and the head 84. When the actuation button 60 is in a first non-actuated operational state, the upper latch 62 of the actuation button 60 is received in the recess 49 of the needle hub 40 and the hub flange 48 is engaged with an undersurface of the upper latch 62. The lower latch 66 of the actuation button 60 is received in the undercut 83 formed between the column 82 of the infusion set base 80 and head 84. Also in the first state, a spring 58 encircles the plurality of ribs 54 of the needle hub 40. The plurality of ribs 54 are like a cylinder and as an alternative a cylinder form may be used in place of the plurality of ribs 54. The spring 58 is captured between the collar 44 of the needle hub 40 and the upper latch 62 of actuation button 60. The engagement between the hub flange 48 and the undersurface of the upper latch 62 causes the hub collar 44 to maintain compression of the spring 58 against the upper latch 62 of the actuation button 62, thereby limiting movement of the needle hub 40 relative to the actuation button 60.

Figure 3:
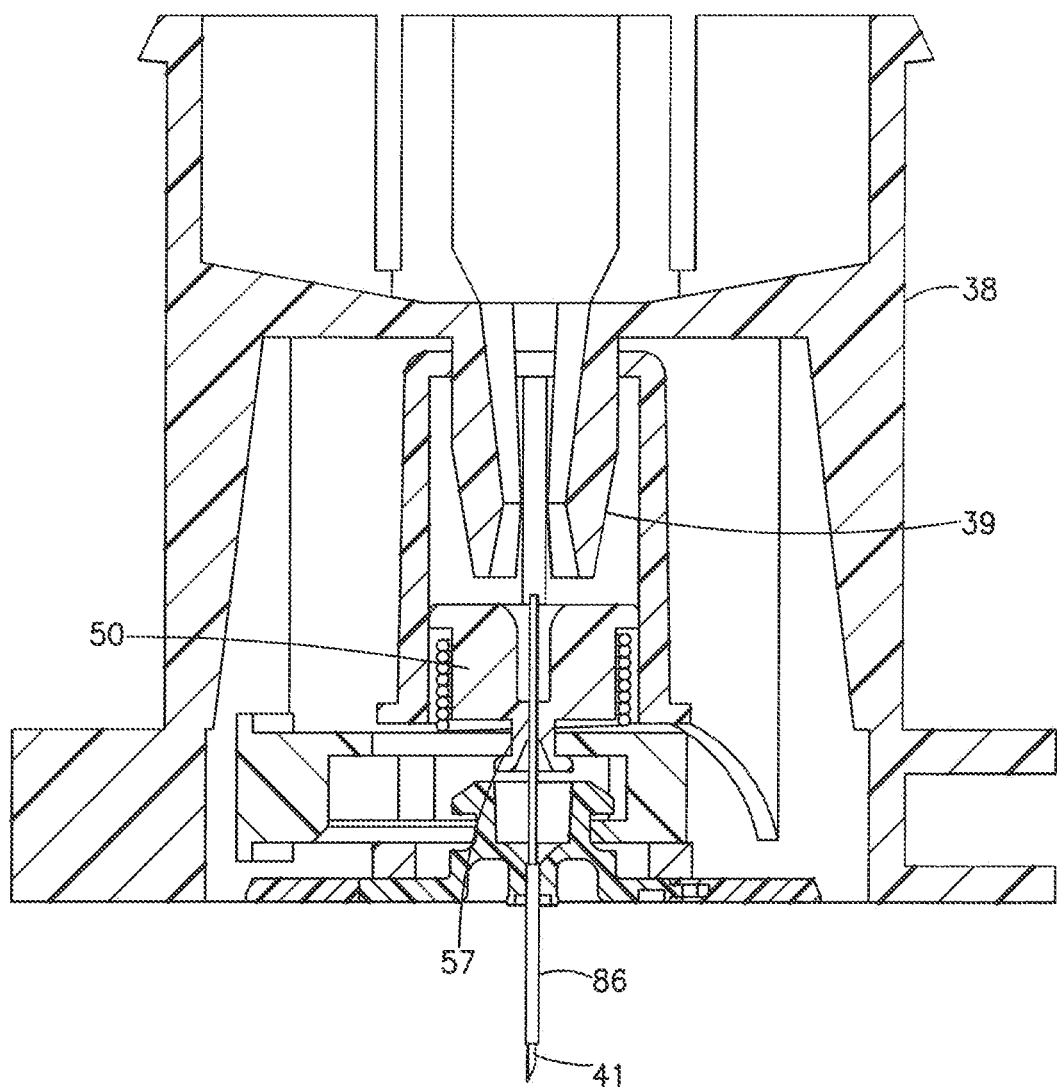
FIG. 3 is a cross-sectional view of the needle stick prevention device of FIG. 1 in a first operational state with the base of FIG. 1 and an insertion device.

FIG. 3 illustrates an insertion device 38 engaged with the needle stick prevention device 10 and infusion set base 80 to facilitate insertion the infusion set base 80 into a patient. With the actuation button 60 in the first operational state, protrusions 39 of the insertion device 38 are received in the proximal opening 24 of the needle shield 20. When the insertion device 38 is mounted in the needle shield 20, the actuation button cannot be actuated. After the needle 41 and a cannula 86 of the infusion set base 80 are inserted into the patient's skin, the insertion device 38 can be removed so that the actuation button 60 can be actuated.

Figure 4:
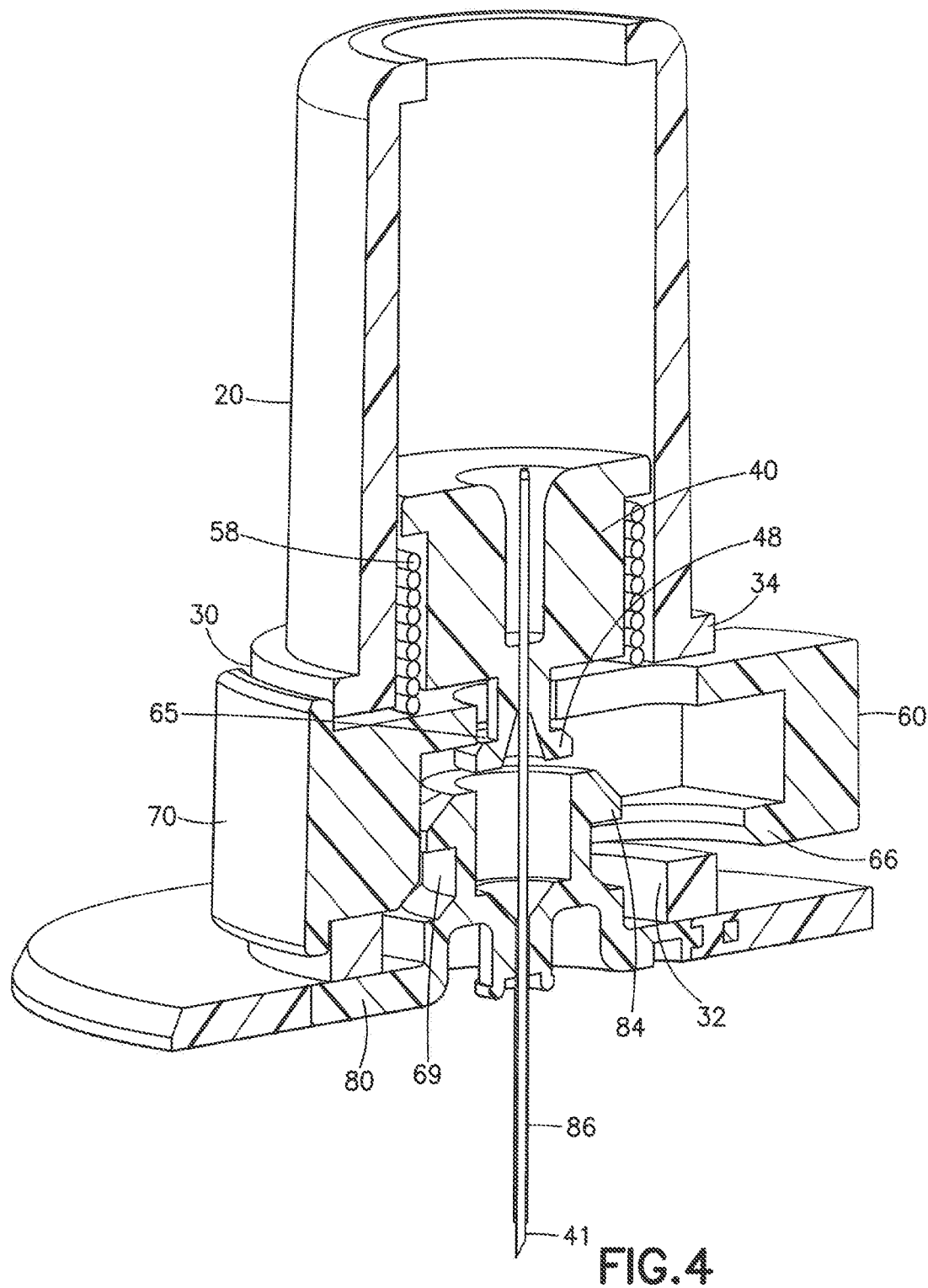
FIG. 4 is a cross-sectional view of the needle stick prevention device of FIG. 1 in a second operational state and the base of FIG. 1.

FIG. 4 illustrates the actuation button 60 in a second actuated operational state after the actuation button 60 is advanced within the transverse opening 32 in a direction to unlock the base 80 and unlock the needle hub 40. Preferably, this direction is substantially perpendicular to the longitudinal axis of the needle hub 40, to the second actuated state. The actuation button 60 is advanced through the transverse opening 32 until the button head 70 engages the outer wall 30 of the needle shield 20 preventing further movement of the actuation button 60 in the actuating direction. According to one embodiment, the button head 70 is sized and dimensioned to be larger than the transverse opening 32.

As also shown in FIG. 4, in the second actuated state, the infusion set head 84 is received in the unlocking portion 69 of the actuation button lower latch 66, and the needle hub flange 48 is simultaneously received in the unlocking portion 65 of the actuation button upper latch 62. The respective unlocking portions 65, 69 of the upper and lower latches are larger than the head 84 and the flange 48 on the needle hub 40.

Figure 6:
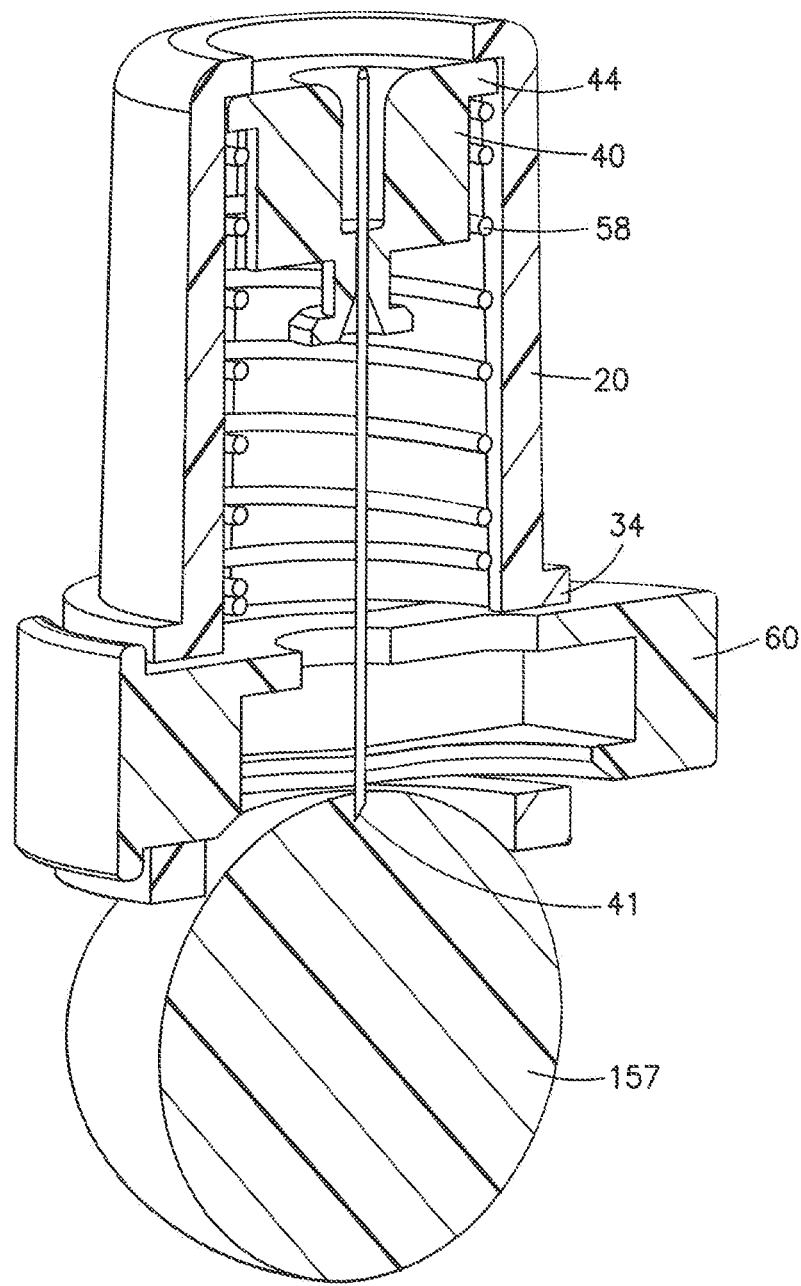
FIG. 6 is a cross-sectional view of the needle stick prevention device of FIG. 1 but with the infusion set base omitted for clarity.

In the second state, the needle 41 can be retracted into the needle shield 20 to a safety or retracted state such as shown in FIG. 6 via operation of the actuation button 60. The unlocking portion 65 of the upper latch 62, as noted earlier, is large enough for passage therethrough of the flange 48 of the needle hub 40. Therefore the movement of the needle hub 40 relative to the actuation button 60 or the needle shield 20 is no longer limited and the force of the spring 58 is no longer restrained. As a result, the spring 58 moves the needle hub 40 proximally through the needle shield passageway 33 to the state shown in FIG. 6. Accordingly, a user is provided with a mechanism to protect from an accidental needle stick.

Also in the second state, the infusion set base 80 may be removed from the needle shield 20 and actuation button 60 by passing the head 84 through the unlocking portion 69 of the lower latch 66. In other words, a user can lift the needle stick prevention device 10 from the base 80 because the actuation button 60 no longer engages the undercut 83 of the base 80.

Figure 7:
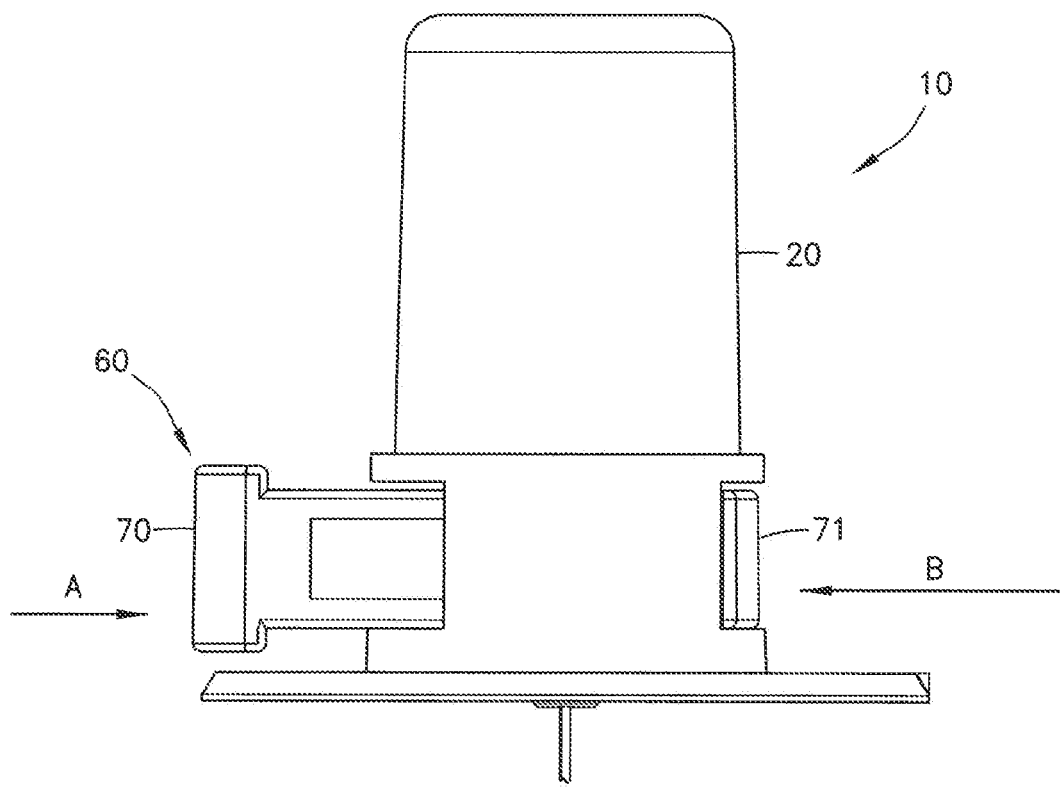
FIG. 7 is a rear view of the needle stick prevention device of FIG. 1 in the first operational state.

FIG. 7 illustrates a rear view of the needle stick prevention device 10. Rather than simply pressing the button head 60 in direction A to actuate the needle stick prevention device 10, a user may engage the button head 60 and the wall 71 simultaneously. As shown in FIG. 7, this simultaneous engagement may produce opposing forces as indicated by arrows A and B acting upon the actuation button 60. These opposing forces may result in no motion of the actuation button 60 relative to the needle shield 20. To reduce the likelihood of this occurring, the actuation button 60 may be modified to prevent the effect of opposing forces being applied to the actuation button 60 for example, as shown in the embodiment illustrated in FIGS. 8-15.

Figure 8:
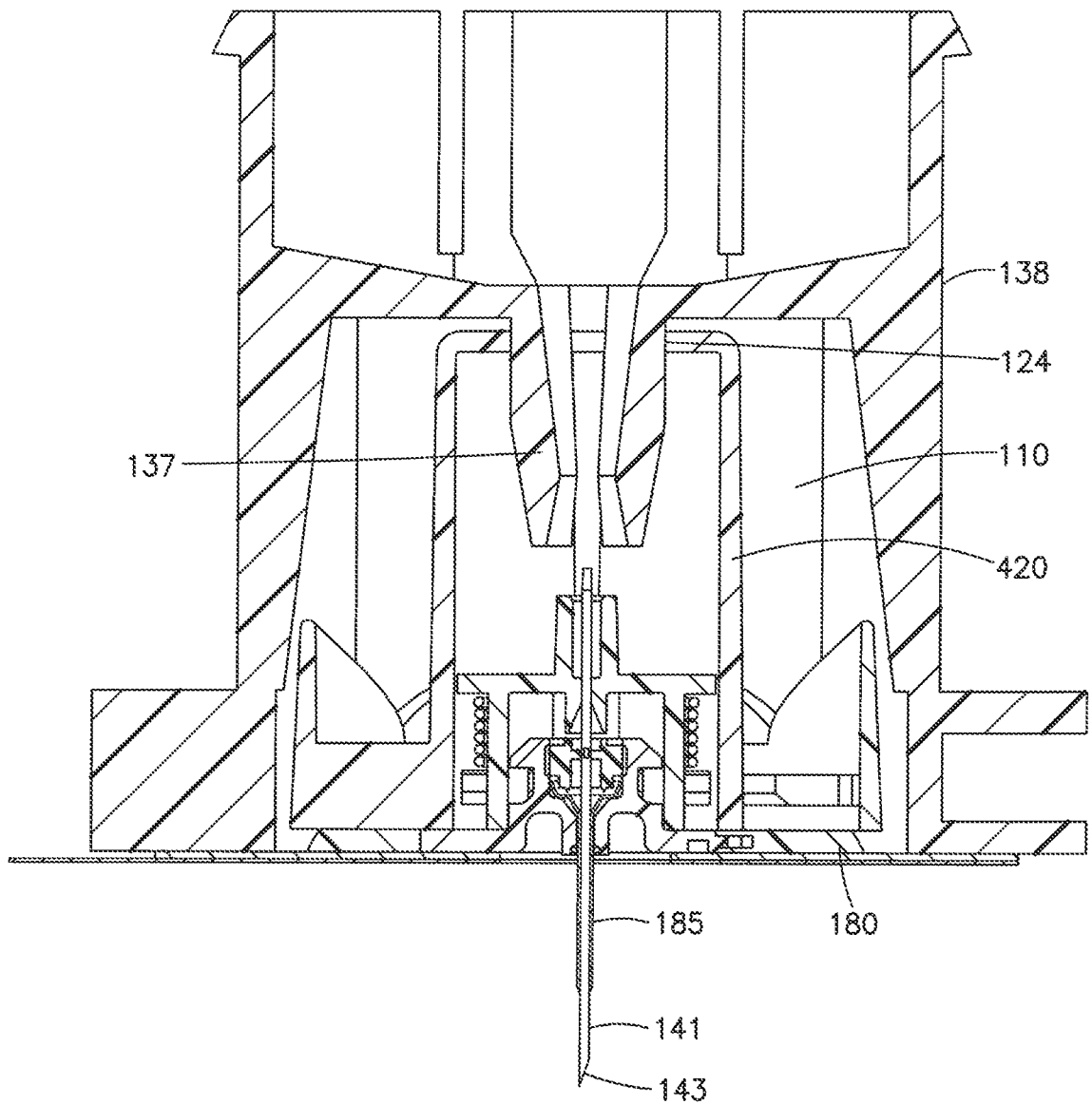
FIG. 8 is a cross-sectional view of the needle stick prevention device for an insertion needle, and an infusion set base in accordance with another embodiment of the present invention, along with an insertion device.
Figure 9:
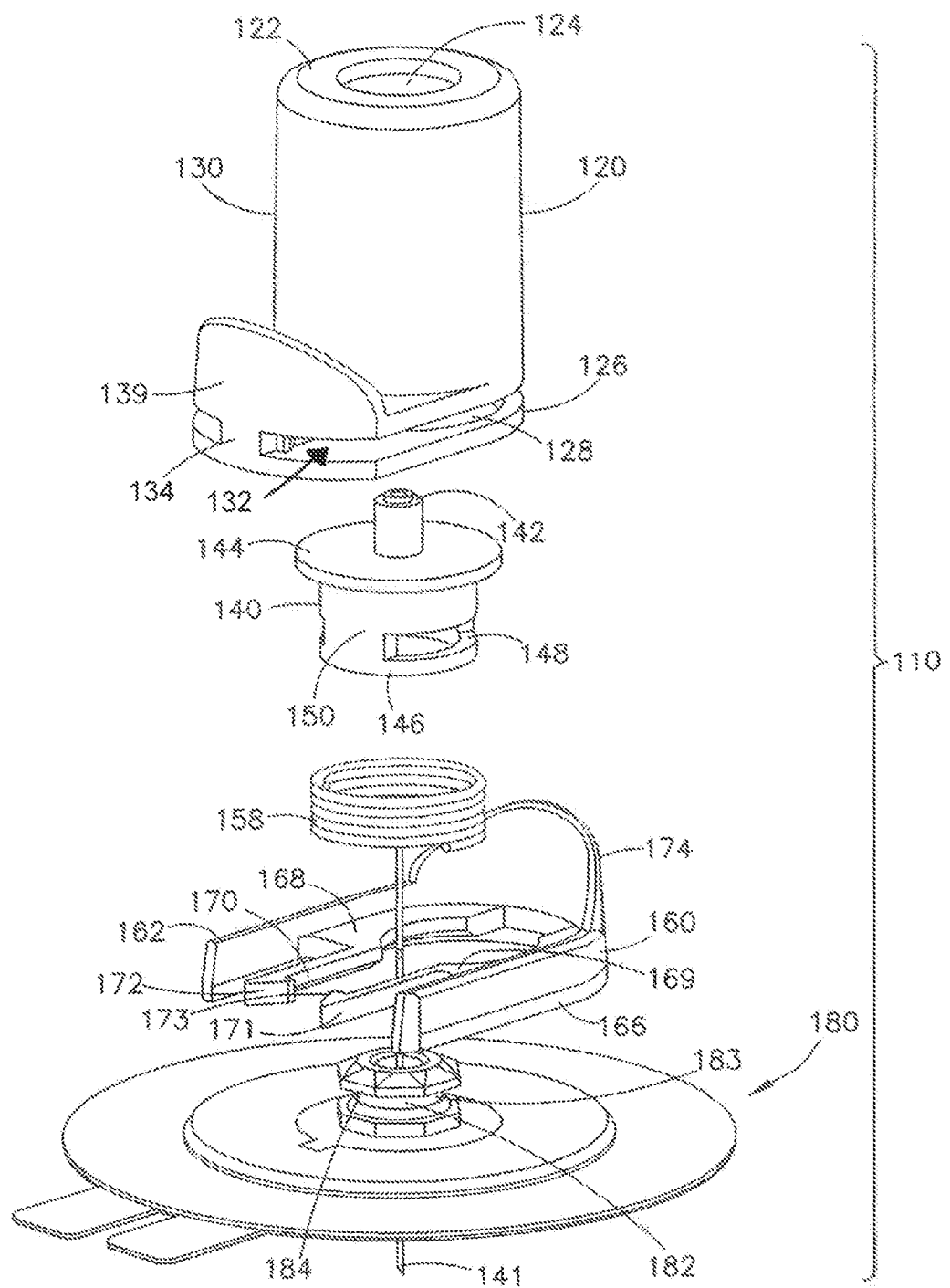
FIG. 9 is an exploded perspective view of the needle stick prevention device of FIG. 8.

FIGS. 8-15 illustrate an embodiment of the invention that includes an actuation shield. FIG. 9 is an exploded view of the needle stick prevention device 110 according to a second embodiment of the invention. As shown, the needle shield 120 for selectively covering a distal end of a needle 141 includes a circumferential outer wall 130 with a proximal end 122 and a distal end 126. The proximal end 122 includes a proximal opening 124 and the distal end 126 includes a distal opening 128. A transverse opening or receptacle 132 is disposed at the distal end and communicates with the distal opening 128. As shown in FIG. 9, in the region of the transverse receptacle 132, the needle shield 120 includes a stationary shroud 139 extending laterally. A passageway 133 is formed by the outer wall 130 and extends between the proximal opening 124 and the distal opening 128.

Movably received within the needle shield passageway 133 is a needle hub 140. The needle hub 140 includes a proximal end 142 and a distal end 146 with a cylindrical hub body 150 extending therebetween. In this embodiment, the cylindrical hub body 150 has a larger diameter than the corresponding hub body of FIGS. 1-7 so that the ribs 54 are not required. According to one embodiment, a needle 141 is received in an inner passageway 157 of the hub body 150. The needle hub 140 also includes a collar 144 located proximal to the proximal end 142 and a transverse opening 148 located at the distal end 146.

Figure 10:
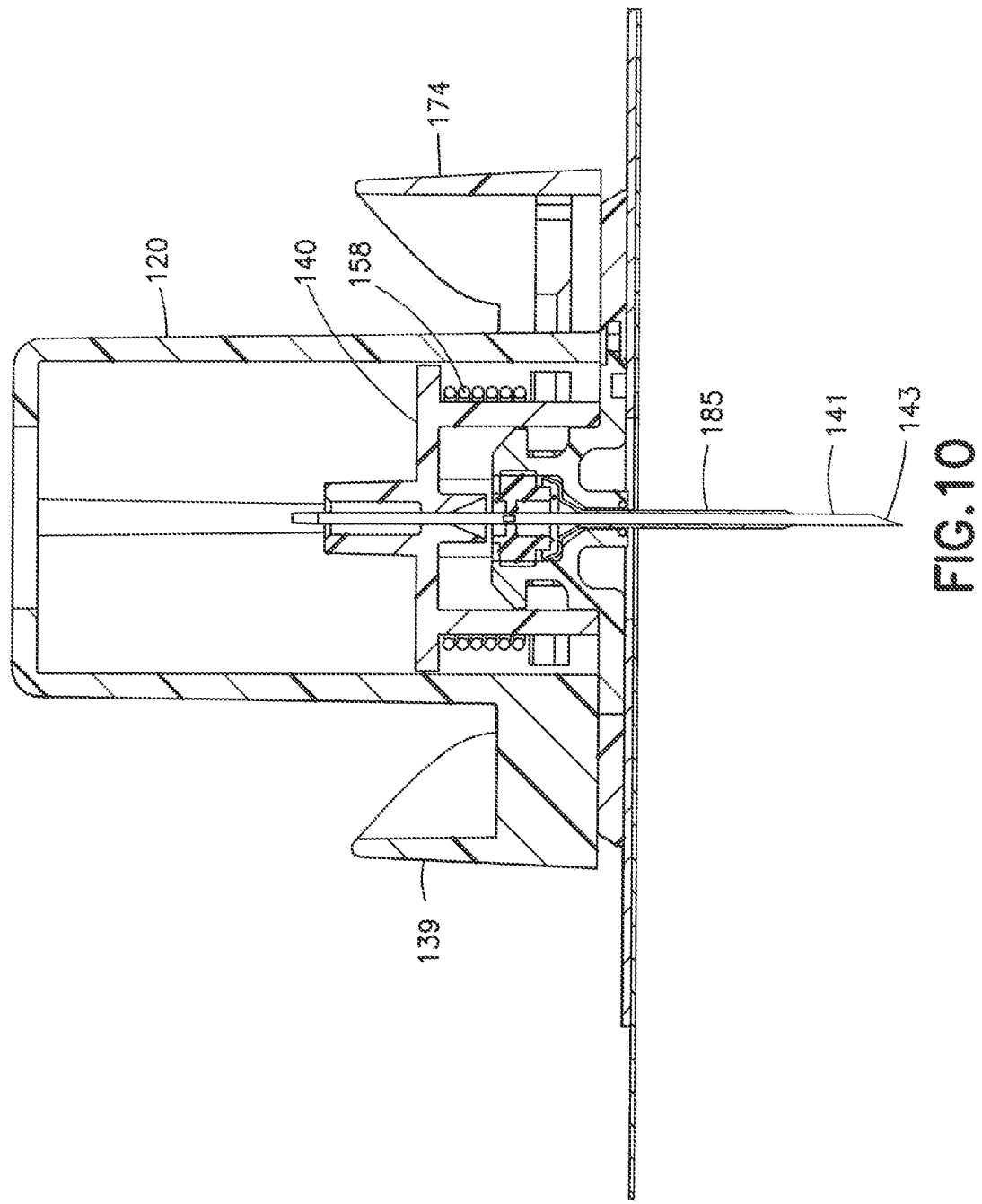
FIG. 10 is a cross-sectional view of the needle stick prevention device of FIG. 8 in a first operational state.
Figure 12:
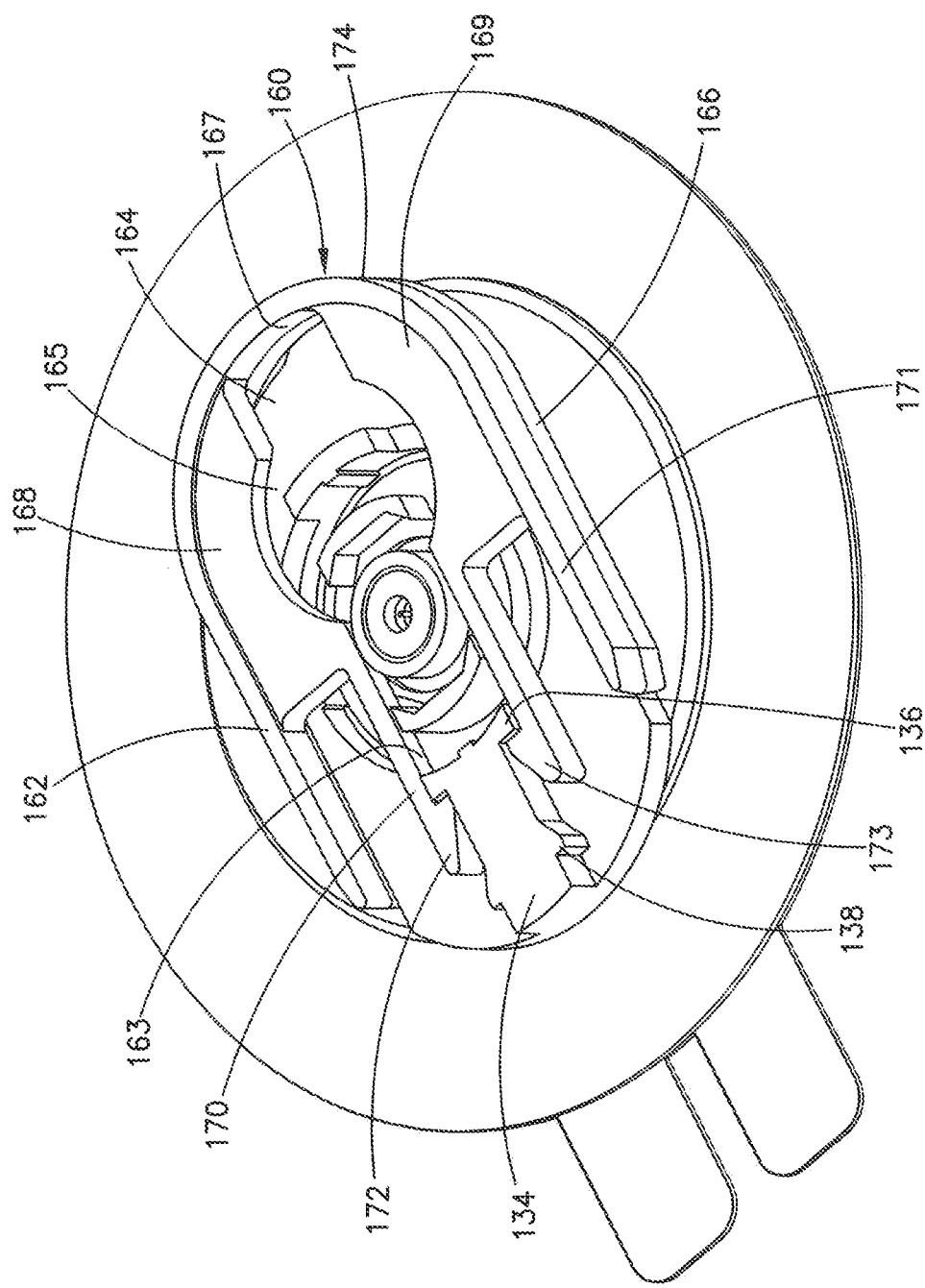
FIG. 12 is a cross-sectional top view of the needle stick prevention device of FIG. 8 in the first operational state.

As illustrated in FIGS. 8-10, a movable actuation button or plug 160 includes a first arm 162 connected to a second arm 166. The movable actuation plug 160 includes an actuation plug shroud 174 actuated by a user to advance the actuation plug 160 into the transverse receptacle 132 of the needle shield 120. A first arcuate member 168 is disposed on an inner surface of the first arm 162, and the first arcuate member 168 includes a first cantilevered arm 170 extending therefrom with a first projection 172 on a free end of the first cantilevered arm 170. A second arcuate member 169 is disposed on an inner surface of the second arm 166, and the second arcuate member 169 includes a second cantilevered arm 171 extending therefrom with a second projection 173 on a free end of the second cantilevered arm 171. As shown in FIG. 12, the first arcuate member 168 and second arcuate member 169 form a substantially keyhole shape 164 within the actuation plug 160. The keyhole shape 164 includes a first portion 163 and a second portion 165, where the first portion is configured to removably lock the needle hub relative to the needle shield. The second state is configured to unlock the needle hub and allow the needle hub to move within the needle shield.

Figure 11:
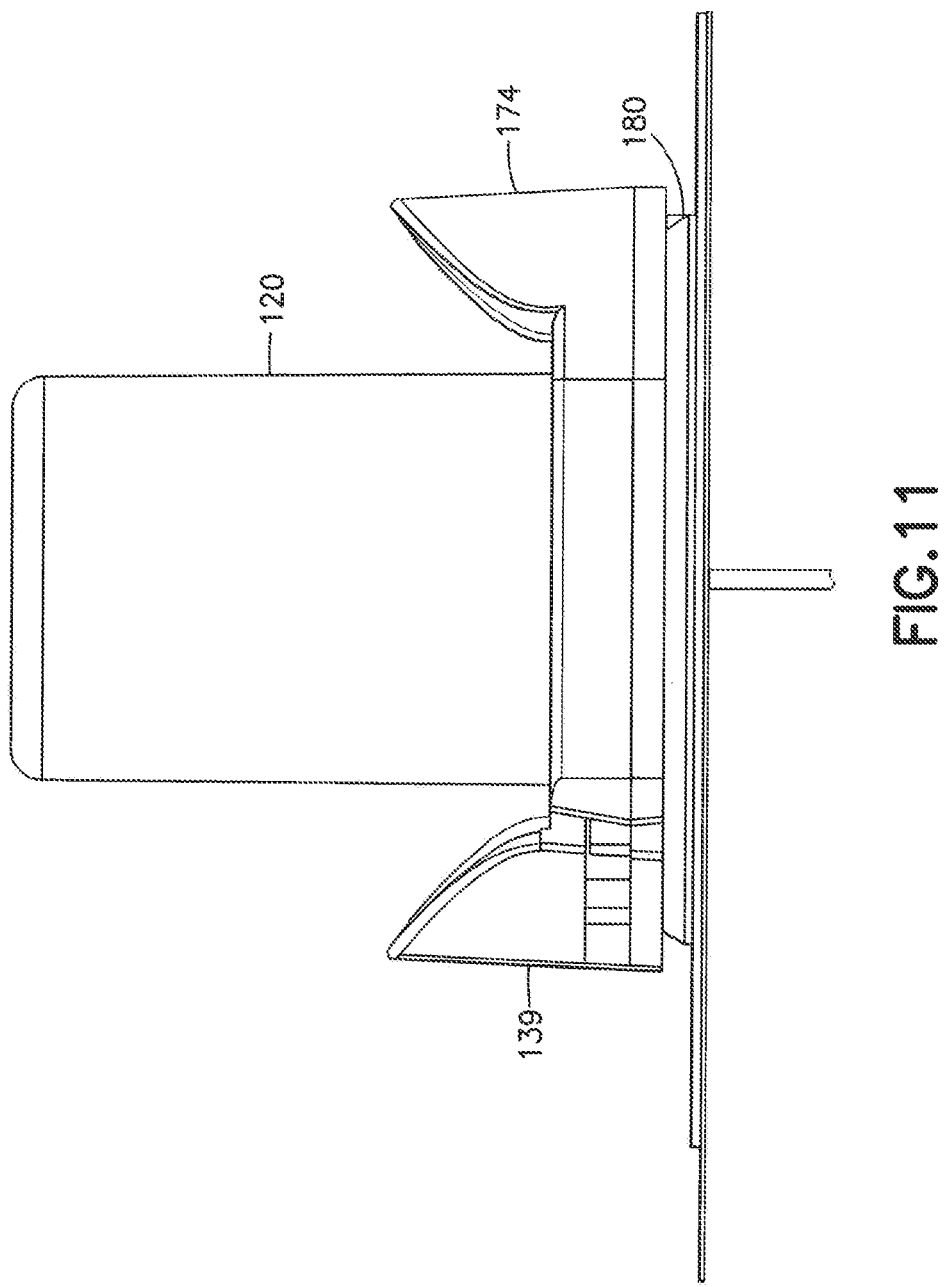
FIG. 11 is a rear view of the needle stick prevention device of FIG. 1 in the first operational state.

An infusion set base 180 can be removably engaged with the actuation plug 160 via an undercut 183 formed between a column 182 extending from the infusion set base 180 and a head 184 formed on the column 182. FIGS. 10-12 illustrate the actuation plug 160 in a first, non-actuated state. In the first state the first and second cantilever arms 170, 171 of the actuation plug 160 are received in the transverse opening 148 of the needle hub 140. The first and second cantilever arms 170, 171 are additionally received in the undercut 183 formed between the column 182 of the infusion set base 180 and the head 184. Also in the first state, a spring 158 surrounds the needle hub 140 and the spring 158 is captured between the collar 144 of the needle hub 140 and an upper surface of the first and second cantilever arms 170, 171. Insertion of the first and second cantilever arms 170, 171 into the transverse opening 148 of the needle hub 140 causes the hub collar 144 to compress the spring 158 against the upper surface of the first and second cantilever arms 170, 171. Thereby limiting movement of the needle hub 140 relative to the needle shield 120.

FIG. 8 illustrates an insertion device 138 engaged with the needle stick prevention device 110 and infusion set base 180 to facilitate insertion a cannula 185 of the infusion set base 180 into a patient. With the actuation button 160 in the first state, protrusions 137 of the insertion device 138 are received in the proximal opening 124 of the needle shield 120. After the needle 141 and a cannula 185 of the infusion set base 180 are inserted into the patient's skin, the insertion device 138 can be removed so that the actuation plug 160 can be actuated.

Figure 13:
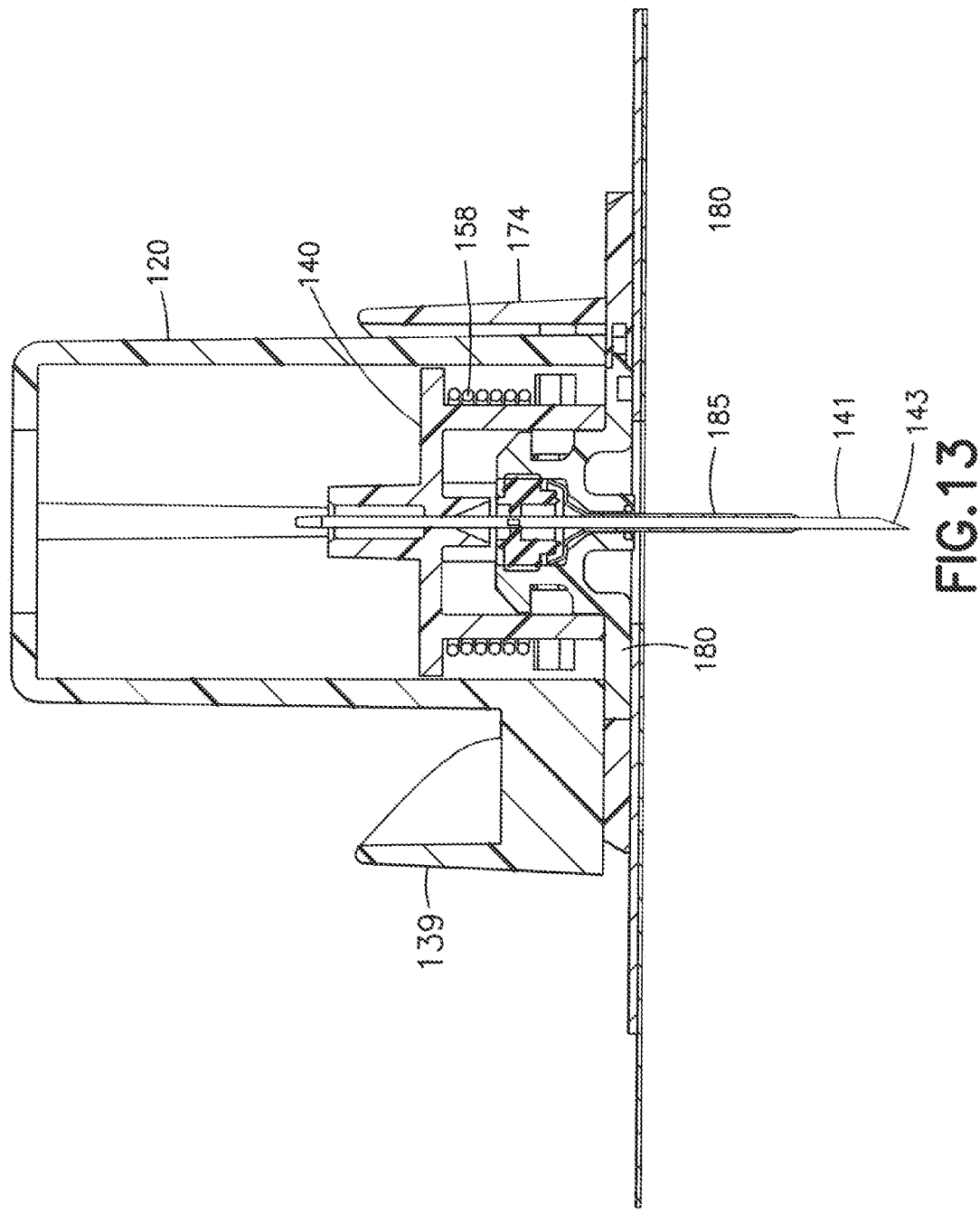
FIG. 13 is a cross-sectional view of the needle stick prevention device of FIG. 8 in the second operational state.
Figure 14:
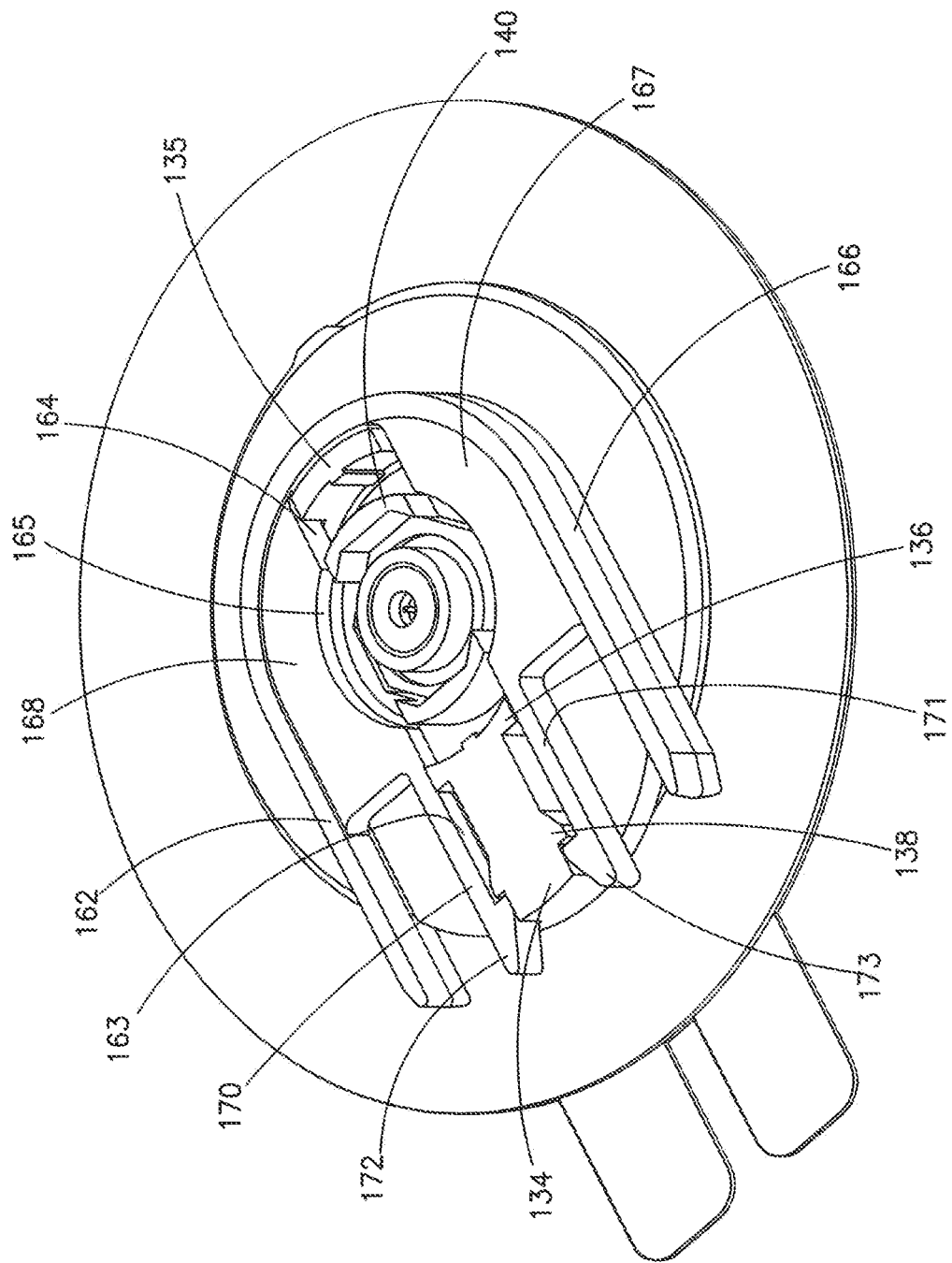
FIG. 14 is a cross-sectional top view of the needle stick prevention device of FIG. 8 in the second operational state.

FIGS. 13 and 14 illustrate the actuation plug 160 in a second, actuated state after the actuation plug 160 is advanced within the transverse opening 132 in a first direction to release the base 180 and facilitate movement of the needle hub 140 relative to the needle shield 120. Preferably, this direction is substantially perpendicular to the longitudinal axis of the needle 141. As a user advances the actuation plug 160 through the transverse opening 131 of the needle shield, the cantilever arms 170, 171 flex outward as the projections 172, 173 move over the sloped portion of detents 138 disposed on the mating portion 134 of the needle shield 120. At the end of the travel of the actuation plug 160 the projections 172, 173 snap inward engaging the flat portion of the detent. This engagement of the projections 172, 173 with the flat portion restricts movement of the actuation plug 160 in a reverse direction. According to one embodiment, a wall 135 diametrically opposed to the mating portion 134 of the needle shield 120 abuts against the inner surface of the actuation plug 160 and prevents further lateral movement of the actuation plug 160 in the first direction within the transverse receptacle 132.

As also shown in FIG. 14, in the second, actuated state, the infusion set head 184 is received in the second portion 165 of the actuation plug keyhole shape 164, and the needle hub collar 144 is simultaneously received in the second portion 165.

Figure 15:
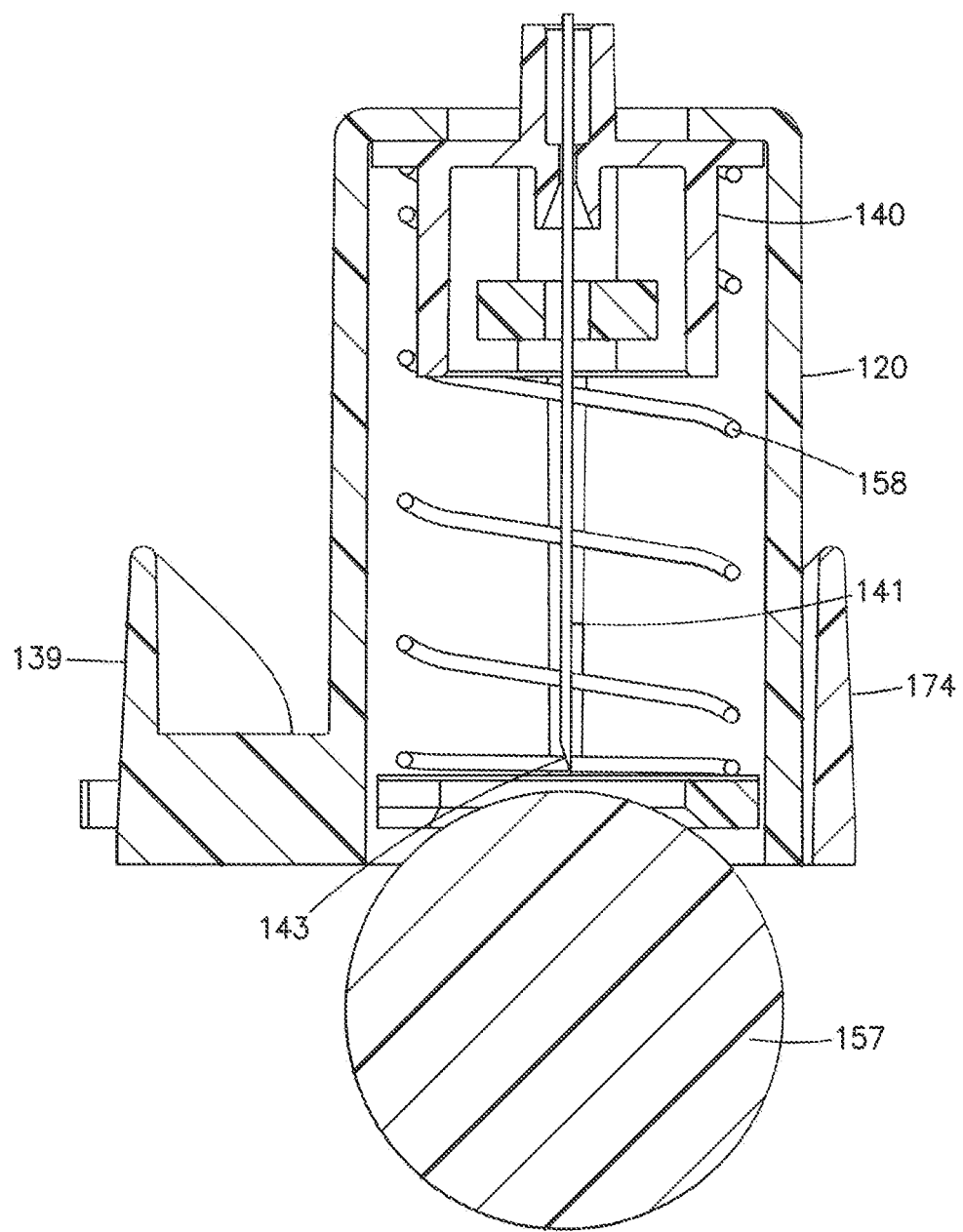
FIG. 15 is a cross-sectional view of the needle stick prevention device of FIG. 8 but with the infusion set base omitted for clarity.

In the second state, the needle 141 can be retracted into the needle shield 120 to a safety or retracted position, such as is shown in FIG. 15, via advancement of the actuation plug 160. The second portion 165 of the keyhole 164 disposed in the actuation plug 160 is large enough for passage therethrough of the collar 144 of the needle hub 140. Therefore the movement of the needle hub 140 relative to the actuation plug 160 is no longer limited, and the spring 158 is no longer restrained. As a result, the spring 158 moves the needle hub 140 proximally through the needle shield passageway 133 to the position shown in FIG. 15. The needle shield 120 surrounds and conceals the needle tip 143 so that an average finger, represented by sphere 157, will not fit through the distal opening 128 of the needle shield. Therefore, a user is provided with a mechanism to protect from an accidental needle stick. Also, in the second state, the needle shield 120 and actuation plug 160 may be removed from the infusion set base 180 by passing the second portion 165 of the keyhole shape over the head 184 of the base 180.

It will be appreciated by those skilled in the art that changes may be made to the embodiments described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The invention claimed is:

1. A combination, comprising:
a needle stick prevention device; and
a medical device including a base, the base having a column extending proximally from the base, and a head extending from the column forming an undercut between the base and the head;
wherein the needle stick prevention device comprises:
a needle shield for selectively covering a distal end of a needle including an outer wall with a passageway communicating with a proximal end of the needle shield and a distal end of the needle shield, wherein the distal end of the needle shield includes a transverse opening communicating with a distal opening extending through the distal end of the needle shield;
a needle hub movably received within the passageway of the needle shield, the needle hub including:
a proximal end;
a distal end; and
the needle, wherein the needle is fixedly connected to the distal end of the needle hub;
an actuation button movably received in the transverse opening of the needle shield to selectively engage the needle shield, the needle hub and the medical device; and a spring disposed between the needle hub and the actuation button, wherein in a first state, the spring is held in a compressed state between the needle hub and the actuation button and the medical device is releasably locked with the actuation button, and in a second state after the actuation button is actuated, the needle stick prevention device is removable from the medical device, the spring is released, and the needle hub is movable relative to the needle shield.

2. The combination of claim 1, wherein the needle stick prevention device further comprises a plurality of ribs or a cylinder disposed between the proximal end and of the needle hub distal end of the needle hub, wherein the spring surrounds the plurality of ribs or the cylinder.

3. The combination of claim 1, wherein the needle stick prevention device further comprises a collar disposed at the proximal end of the needle hub.

4. The combination of claim 3, wherein the spring is compressed between the collar and the actuation button in the first state.

5. The combination of claim 1, wherein in the first state, the actuation button engages the needle hub and the base.

6. The combination of claim 1, wherein in the second state, the actuation button releases the needle hub and the base from engagement with the actuation button.

7. A combination, comprising:
a needle stick prevention device; and
a medical device including a base, the base having a column extending proximally from the base, and a head extending from the column forming an undercut between the base and the head;
wherein the needle stick prevention device comprises:
a needle shield for selectively covering a distal end of a needle including an outer wall with a passageway communicating with a proximal end and a distal end of the needle shield, wherein the proximal end of the needle shield includes a proximal opening and the distal end includes a transverse receptacle communicating with a distal opening extending through the distal end of the needle shield;
a needle hub movably received within the passageway of the needle shield, the needle hub including:
a proximal end;
a distal end;
the needle, wherein the needle is fixedly connected to the distal end of the needle hub; and
a transverse opening disposed proximal to the distal end of the needle hub;
an actuation button movably received in the transverse opening of the needle hub and the transverse receptacle of the needle shield to engage the needle shield, the needle hub, and the medical device with the head of the medical device being inserted through the distal opening of the needle shield; and
a spring disposed between the needle hub and the actuation button, wherein in a first state the spring is held in a compressed state between the needle hub and the actuation button, the needle hub is not movable relative to the needle shield and the medical device is releasably locked with the actuation button, and in a second state after the actuation button is advanced into the transverse receptacle, the needle stick prevention device is removable from the medical device, the spring is released, and the needle hub is movable relative to the needle shield.

8. A combination, comprising:
a needle stick prevention device; and
a medical device including a base, the base having a column extending proximally from the base, and a head extending from the column forming an undercut between the base and the head;
wherein the needle stick prevention device comprises:
a needle shield for selectively covering a distal end of a needle including an outer wall with a passageway communicating with a proximal end of the needle shield and a distal end of the needle shield, wherein the proximal end of the needle shield includes a proximal opening and the distal end of the needle shield includes a transverse opening communicating with a distal opening extending through the distal end of the needle shield;
a needle hub movably received within the passageway of the needle shield, the needle hub including:
a proximal end;
a distal end;
the needle, wherein the needle is fixedly connected to the distal end of the needle hub; and
a button engaging portion;
an actuation button movably received in the transverse opening of the needle shield to selectively engage the needle shield, the button engaging portion, and the medical device with the head of the medical device being inserted through the distal opening of the needle shield; and
a spring disposed between the needle hub and the actuation button, wherein in a first state the spring is held in a compressed state between the needle hub and the actuation button, the needle hub is not movable relative to the needle shield, and the medical device is releasably locked with the actuation button, and in a second state after the actuation button is advanced into the transverse opening, the needle stick prevention device is removable from the medical device, the spring is released, and the needle hub is movable relative to the needle shield.

* * * * *